US006302942B1

(12) United States Patent
Ma et al.

(10) Patent No.: US 6,302,942 B1
(45) Date of Patent: *Oct. 16, 2001

(54) METHODS FOR REMOVING POLLUTANTS FROM CONTAMINATED SOIL MATERIALS WITH A FERN PLANT

(75) Inventors: Lena Q. Ma; Ken M. Komar, both of Gainesville; Elizabeth D. Kennelley, Archer, all of FL (US)

(73) Assignee: University of Florida, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/546,941

(22) Filed: Apr. 11, 2000

Related U.S. Application Data

(63) Continuation-in-part of application No. 09/471,566, filed on Dec. 23, 1999.
(60) Provisional application No. 60/129,203, filed on Apr. 14, 1999.

(51) Int. Cl.[7] .............................. C22B 3/18; C22B 3/24
(52) U.S. Cl. .............................. 75/712; 75/710; 75/711; 210/602; 47/58.1; 800/295
(58) Field of Search ............................ 75/711, 712, 710; 210/602

(56) References Cited

U.S. PATENT DOCUMENTS

| 5,000,852 | * | 3/1991 | Tel-Or et al. ..................... 210/602 |
| 5,364,451 | | 11/1994 | Raskin ................................. 75/710 |
| 5,785,735 | * | 7/1998 | Raskin et al. ....................... 75/711 |
| 5,809,693 | * | 9/1998 | Chet et al. ........................... 47/58 |
| 5,917,117 | | 6/1999 | Ensley ................................. 75/722 |
| 5,927,005 | | 7/1999 | Gardea-Toresdey .............. 47/58.1 |
| 5,944,872 | | 8/1999 | Chaney ............................... 75/712 |
| 6,005,092 | | 12/1999 | Shoseyov ......................... 536/23.6 |

OTHER PUBLICATIONS

Ho et al. Bull. Environ. Contam. Toxicol. vol. 35, pp. 430–438, 1985.*
Noctor et al. Journal of Experimental Botany, vol. 49, No. 321, pp. 623–647, Apr. 1998.*
Blaylock, et al., Enhanced Accumulation of pH in Indian Mustard by Soil–Applied Chelating Agents, *Environ.Sci Technol.* 1997, 31, p 860–865.
Pickering, et al., Reduction and Coordination of Arsenic in Indian Mustard, *Plant Physiology,* Apr. 2000, vol. 122, p 1171–1177.
Bennett, F.A., E.K. Tyler, R.R. Brooks, P.E.H. Gregg, and R.B. Stewart (1998). Fertilisation of Hyperaccumulators to Enhance their Potential for Phytoremediation and Phytomining. *Plants that Hyperaccumulate Heavy Metals.* R. R. Brooks. New York, CAB International: 249–259.
Cullen, W.R. and K.J. Reimer (1989). "Arsenic Speciation in the Environment." *Chem. Rev.*(89): 713–764.

Cunningham, S.D., J.R. Shann, D.E. Crowley, and T.A. Anderson (1997). Phytoremediation of Contaminated Water and Soil. Phytoremediation of Soil and Water Contaminants. E.L. Kruger, T.A. Anderson and J.R. Coats. Washington, DC, American Chemical Society: 2–15.
Dix, M.E., N.B. Klopfenstein, J.W. Zhang, S.W. Workman, and M.S. Kim (1997). Potential Use of Populus for Phytoremediation of Environmental Pollution in Riparian Zones.
Ebbs, S.D., M.M. Lasat, D.J. Brady, J. Cornish, R. Gordon, and L.V. Kochian (1997). "Phytoextraction of Cadmium and Zinc from a Contaminated Soil." *Journal of Environmental Quality* 26: 1424–1430.
Fowler, B.A. (1977). Toxicology of Environmental Arsenic. *Toxicology of Trace Elements.* R.A. Goyer and M.A. Mehlman. New York, NY, Hemisphere Publishing Corporation. 2: 79–122.
Grant, C. and A.J. Dobbs (1977). "The Growth and Metal Content of Plants Grown in Soil Contaminated by a Copper/Chrome/Arsenic Wood Preservative." *Environ. Pollut.* 14: 213–226.
Huang, J.W., M.J. Blaylock, Y. Kapulnik, and B.D. Ensley (1998). "Phytoremediation of Uranium–Contaminated Soils: Role of Organic Acids in Triggering Uranium Hyperaccumulation in Plants." *Environ. Sci. Technol.* 32: 2004–2008.
Kramer, U., R.D. Smith, W.W. Wenzel, I. Raskin, and D.E. Salt(1997). "The Role of Metal Transport and Tolerance in Nickel Hyperaccumulation by Thlaspi goesingense Halacsy." *Plant Physiol.*(115): 1641–1650.
Lasat, M.M., M. Fuhrmann, S. D. Ebbs, J. E. Cornish, and L. V. Kochian (1998). "Phytoremediation of a Radiocesium–Contaminated Soil: Evaluation of Cesium–137 Bioaccumulation in the Shoots of Three Plant Species." *Journal of Environmental Quality* 27: 165–169.
Ma, L.Q., F. Tan, and W.H. Harris. 1997. Concentration and distribution of 11 elements in Florida soils. J. Environ. Qual. 26: 769–775.
McGrath, S.P. (1998). Phytoextraction for Soil Remediation. Plants that Hyperaccumulate Heavy Metals. R.R. Brooks. New York, NY, CAB International: 261–287.
Porter, E.K. and P.J. Peterson (1977). Arsenic Tolerance in Grasses Growing on Mine Waste. *Environ. Pollut.* 14: 255–265.

(List continued on next page.)

*Primary Examiner*—Amy J. Nelson
*Assistant Examiner*—Medina A. Ibrahim
(74) *Attorney, Agent, or Firm*—Brian S. Steinberger; Law Offices of Brian S. Steinberger

(57) ABSTRACT

The invention provides processes and materials for phytoremediating materials which has been contaminated with arsenic, phosphorous, or other metals. In a preferred embodiment, the subject invention provides fern plants, which accumulate arsenic from contaminated materials. The fern plants efficiently remove arsenic from the materials. The fern plants can be harvested and readily disposed of, or can be treated to recover arsenic.

50 Claims, 1 Drawing Sheet

OTHER PUBLICATIONS

Squibb, K.S. and B.A. Fowler (1983). The Toxicity of Arsenic and its Compounds. *Biological and Environmental Effects of Arsenic*. B.A. Fowler. Research Triangle Park, NC, Elsevier Science Publishers: 233–269.

Walsh, L.M. and D.R. Keeney (1975). Behavior and Phytotoxicity of Inorganic Arsenicals in Soils. *Arsenical Pesticides*. E. A. Woolson. Washington, D.C., ACS: 35–52.

* cited by examiner

METHODS FOR REMOVING POLLUTANTS FROM CONTAMINATED SOIL MATERIALS WITH A FERN PLANT

This invention relates to compositions and methods of phytoremediation using fern plants for removing contaminated substances such as arsenic and phosphorus, from polluted materials, such as soils, sediments, wastes and water. This application is a continuation-in-part (CIP) of U.S. Ser. No. 09/471,566, filed Dec. 23, 1999, which claims priority from provisional application U.S. Ser. No. 60/129,203, filed Apr. 14, 1999.

BACKGROUND OF THE INVENTION

Arsenic is a major contaminant of soils, sediments, wastes, and water in the United States and in foreign countries. Contamination of soils results from, for example, pesticides and wood treatments. Not only is arsenic a prevalent contaminant but it is also particularly dangerous because it is a known carcinogen. Currently there is no cost effective and efficient way to clean up sites contaminated with arsenic.

The use of arsenic in agricultural and industrial processes has resulted in numerous contaminated sites in Florida. During the early part of the 20th century, arsenic was commonly used as an insecticide component to control disease-carrying ticks on southern cattle so that Florida cattlemen could sell to the northern cattle markets. Arsenic, typically in the form of arsenic pentoxide, was also used in conjunction with copper sulfate and sodium or potassium dichromate as a wood preservative which is known as the copper/chromium/arsenic wood preservative process, (CCA). With both of these processes, the risk of soil contamination from spills and leaks was great. The arsenic level at many of these sites is currently higher than 600 mg/kg even after years of idleness. The typical concentration range in soil is between 0.1 to 40 mg/kg, with a mean concentration of 5–6 mg/kg. The typical range of arsenic in Florida soils is 0.01 to 50.6 mg/kg.

In most soil systems, arsenic is present in many forms of which arsenate is typically the dominant one. In this form, it has properties very similar to phosphate including the formation of insoluble salts with cations and sorption by soil constituents. Because arsenic has a wide range of oxidation states (−3, 0, +3, and +5) it has the ability to form many types of organic and inorganic complexes. At high pH ranges, typically 7 to 9, the arsenic in soils predominantly consists of complex oxyanions of As(V), such as $AsO_2^{-1}$, $AsO_4^{-3}$, $HAsO_4^{-2}$, and $H_2AsO_4^{-1}$. In soils with low pH and low Eh, the predominant forms of arsenic are the arsenites ($H_3ASO_3$).

Although arsenic is commonly found in all natural systems at minute levels, it can be very toxic to both plants and animals at higher concentrations. The toxic effects of arsenic have been known for some time. The exposure of animals to arsenic is second in toxicity only to lead for many farm and household animals. Most cases of arsenic poisoning in animals occur in bovine and feline species as a result of contaminated feed supplies. Other species that are affected are forage-eating animals, such as horses and sheep, that encounter fields that may have been treated with arsenic pesticides. The toxic effects of arsenic to humans and animals can be related to the interactions that occur within the cells of poisoned individuals, especially the mitochondria.

Arsenic is present naturally in almost all plant and tree species in minute amounts. The tolerance of plant and tree species to arsenic varies with species, soil type, and the form of arsenic present in a soil. Over time, a classification scheme was developed to identify the tolerance of vegetables and fruit species (see Table A). In general, the distribution of arsenic in the plant species follows a common trend. Typically, the roots will contain higher concentrations of arsenic than the stems, leaves, and fruits. Some plant species have demonstrated the ability to accumulate elevated arsenic in the above ground portion of the plants. Some species in the Agrostis genus had the ability to accumulate up to 3,460 mg/kg arsenic from soil that contained up to 2.6% arsenic. Other reports have demonstrated the ability of Douglas fir, *Pseudotsuga menziesii*, to accumulate up to 1,000 mg/kg arsenic in biomass, allowing this tree to be used as a biogeochemical indicator for gold, silver, and other ores.

TABLE 1

Arsenic Tolerance of Agronomic Crops

| Tolerance Grouping | Crop Species |
| --- | --- |
| Very Tolerant | Asparagus, potato, tomato carrot, tobacco, dewberry, grape, red raspberry |
| Fairly Tolerant | Strawberry, sweet corn, beet, squash |
| Low or No Tolerance | Snap pea, lima bean, onion, pea, cucumber, alfalfa |

Environmental arsenic contamination is of concern due to its biological activities as a teratogen, carcinogen, and mutagen as well as its detrimental effects on the immune system. Due to the concern expressed over arsenic contaminated sites, various remediation techniques have been developed. Methods for remediating arsenic contaminated sites can be performed in situ and ex situ and have varying degrees of complexity, effectiveness, and cost. Due to the lack of effective technologies and the costs associated with the excavation and landfilling of the soil materials, efforts to remediate these arsenic contaminated sites have been minimal. These remediation methods can be divided into three groups: chemical, physical, and biological remediation methods.

One of the biological remediation techniques is phytoremediation. Phytoremediation is a growing technology that utilizes the ability of the plants to accumulate nutrients and trace elements. Phytoremediation is the process of employing plants to remediate contaminated soils. Typically this is done in one of two ways, either by phytostabilization or by phytoextraction. With phytostabilization, plants are used to stabilize contaminated soils by decreasing wind and water erosion as well as decreasing water infiltration and contaminant leaching into groundwater. Phytoextraction attempts to remove contaminants from the rhizosphere through plant uptake and the contaminants are accumulated in roots, leaves and/or stems. The plant materials are then harvested and the contaminants reclaimed from the plant biomass or the materials are disposed of at a hazardous waste facility.

Currently, certain plants have been identified that can be utilized to remediate soil and water systems contaminated with metals, metalloids, petroleum constituents, pesticides, and industrial wastes. Also, many plant species have been identified that accumulate lead, selenium, nickel, zinc, and other metals. For example, U.S. Pat. Nos. 5,364,451 and 5,711,784 describe phytoremediation of metal-containing soils.

For the remediation of contamination sites and/or recovery of precious metals, phytoextraction can be an attractive option. Phytoextraction is the process of removing a contaminant from a system via plant roots for remediational purposes. Originally, the term phytoextraction was applied to the removal of trace elements from soils, but recently new applications have been discovered for this process. One of the newest uses of phytoextraction has been its use in accumulating trace elements of economic value (phytomining), such as gold and nickel.

In some situations, soil amendments and chelating agents can be used to aid in plant growth and in accumulation of trace elements by plants. The soil may have a low pH, poor aeration, inappropriate soil texture, high salinity, etc. To overcome this, agronomic techniques can be used to increase the chance of plant survival. These include addition of organic matter, liming, and fertilization to name a few. In certain situations, addition of soil amendments decreases the quantity of the contaminant that the plant will accumulate but this is typically offset by the increase in biomass that is produced.

For many soil contaminants, chelating agents or organic acids are required to assist in their accumulation by plants. The low solubility of many trace elements and radionuclides is often the limiting factor in metal extraction by plants. For example, lead in soil has a limited solubility and low bioavailability for plant uptake due to complexation with organic matter, sorption on clay and oxides, and precipitation as carbonates, hydroxides, and phosphates.

To overcome this problem, metal-chelating agents can be added. Traditionally, chelates were used in agriculture and horticulture to deliver micronutrients to plants. With the use of chelates in phytoremediation, the chelate is used to increase the bioavailability of the contaminant for plant uptake. There are concerns with the use of chelates though. In some situations, the chelate may have a detrimental effect on plant growth. In one experiment, lead hyperaccumulating plants were grown in contaminated soils for two weeks before the chelating agent, ethlene diamine tetraacetic acid (EDTA) was applied. After one week, the plants were harvested after sustaining significant damage. Other experiments utilizing EDTA to increase the bioavailability of lead for phytoextraction have shown a significant increase in the accumulation of lead by even common agronomic plants.

There are other concerns associated with the use of chelates, in addition to the possible detrimental effect on plant health. Much concern has been expressed over the potential of groundwater contamination. The use of chelates will also increase the cost of a remediation process. Some estimates state that to increase the mobility of one ton of lead in contaminated soil will require approximately one ton of EDTA.

Prior to the subject invention, there has been no plant species identified that can enrich large quantities of arsenic into its biomass from contaminated soils, with arsenic concentration in plant being much greater than that in the soil. Also, prior to the subject invention there has been no report of the use of fern plants in phytoremediation.

SUMMARY OF THE INVENTION

The subject invention pertains to the identification of fern plants, which are able to extract pollutants from contaminated materials. In a preferred embodiment, the pollutant is arsenic.

Pollutants can be removed from materials including, but not limited to, soils, sediments, wastes, and water by the plants of the subject invention which accumulate the pollutants in the biomass of the plant. This is advantageous because these plants can be used to efficiently remediate contaminated materials.

In a preferred embodiment the subject invention provides a method for phytoremediating arsenic-contaminated sites wherein arsenic accumulating fern plants remove arsenic from the contaminated materials. Specifically exemplified herein is the use of the Chinese Ladder Brake fern (*Pteris vittata*). Advantageously, this species can have a total accumulation of arsenic up to and exceeding 5,0001 mg/kg on a dry weight basis.

The fern plants of the subject invention accumulate arsenic in very high concentrations. The plant leaves, stems, and/or roots can then be harvested and readily disposed of, thereby reducing the arsenic content of the contaminated site. Alternatively, arsenic may be recovered from the harvested plants.

The fern plants of the subject invention have many advantageous characteristics for use in phytoremediation. For example, these plants are extremely efficient in extracting arsenic from soils (extremely high arsenic enrichment factor), they grow in many environments, they grow quickly producing a large biomass and they reproduce easily. Also, advantageously, they are perennials which do not need to be replanted each year.

Further objects and advantages of this invention will be apparent from the following detailed description of a presently preferred embodiment, a detailed description of the following examples and the accompanying drawing.

BRIEF DESCRIPTION OF THE EXAMPLES

Example 1 refers to site characterization and plant analysis (Table 2).

Example 2 refers to accumulation and distribution of arsenic, copper and chromium in plant biomass from the CCA contaminated site (Tables 3 and 4).

Example 3 phytoremediation of arsenic contaminated sites using *P. vittata* (Table 4).

Example 4 refers to the effectiveness of arsenic-accumulating plant (*P. vittata*) in contaminated and non-contaminated sites (Tables 5–8).

Example 5 refers to the effectiveness of other arsenic-accumulating fern plants in removing arsenic from arsenic contaminated sites (Tables 9–10).

Example 6 refers to the effectiveness of the Brake fern plant in removing arsenic from different arsenic-contaminated soils (Table 11).

Example 7 refers to the effectiveness of the Brake fern plant in removing arsenic from different arsenic-contaminated wastes (Table 12).

Example 8 refers to the capability of the Brake fern plant in removing arsenic from aqueous solutions (Table 13).

Example 9 refers to the capability of the Brake fern plant in removing arsenic from an artificially contaminated soil containing different levels of arsenic (Table 14).

Example 10 refers to the capability of the Brake fern plant in removing arsenic from an artificially contaminated soil containing different specie of arsenic (Table 15).

Example 11 refers to the importance of growth and time in arsenic accumulation by the Brake fern plant.

Example 12 refers to phosphorus accumulation from the CCA contaminated soil by the Brake fern plant (Tables 16–17).

DESCRIPTION OF THE PREFERRED EMBODIMENT

Figure 1B:
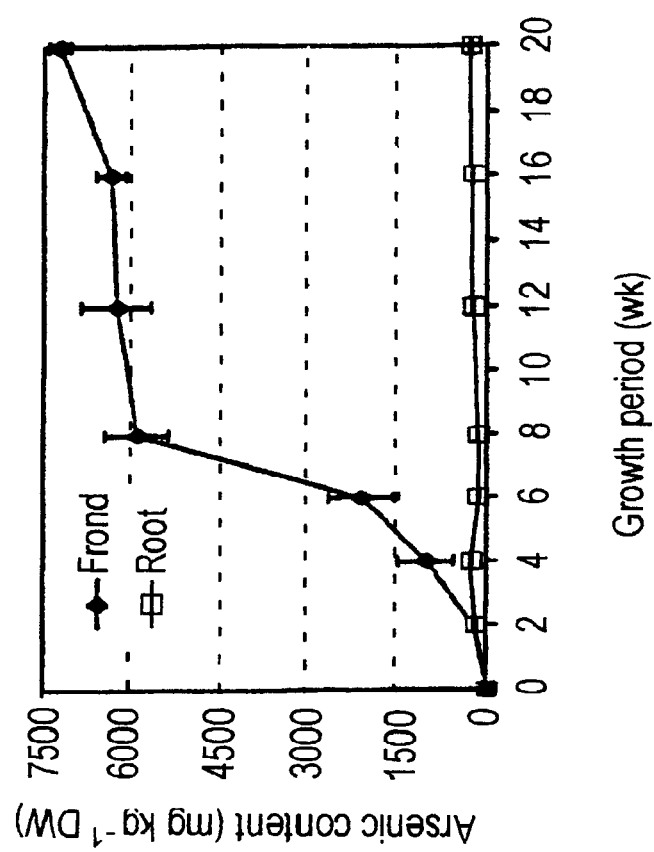
FIG. 1B is a graph of arsenic content vs. growth period of Example 11.

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

The subject invention pertains to the identification of plants that accumulate arsenic in very high concentrations. These plants can be used to remediate arsenic contaminated sites. Plants can also be used according to the subject invention to remove phosphorous from contaminated sites. Preferably, the plants which are used in the remediation methods of the subject invention are fern plants. With the teachings provided herein, the person skilled in the art could, for the first time, utilize fern plants to remove various pollutants. The inorganic pollutants may be bonded to, or otherwise chemically associated with, organic or inorganic compound(s). The pollutants may be, for example, copper, chromium, or phosphorus. Preferably, arsenic is removed. The metals may be, for example, lead, gold, selenium, copper, cadmium, chromium, nickel, or zinc. Preferably, arsenic is removed. The materials from which the pollutant is removed may be any contaminated materials and can exist as solid or liquid form, for example, soils, sediments, wastes, or waters. The wastes include all kinds of wastes regardless of its origin, for example, construction & demolition debris, composts, sewage sludge, ash, sawdust, or recovered screen material. The examples of waters include but not limited to groundwater, surface water, runoff, or waste water. Contaminated wetland can also be treated using this technique.

In a preferred embodiment, the method of the subject invention involves contacting a fern plant with arsenic-containing material and maintaining the plant in the environment under conditions sufficient for the plant to accumulate arsenic from the material. The plant is maintained in the site for a time and under conditions sufficient for the plant to accumulate arsenic in the stems, leaves and/or roots. The plant may be harvested from the site and disposed of.

Arsenic "accumulating" fern plants refer to the ability of the fern plants described herein to perform one, or more, of the following activities: (i) transporting arsenic from soil or waste particles and/or liquid into the roots and/or other tissues; (ii) physical and/or chemical sorption of arsenic to the root biomass; and (iii) prevention or inhibition of leaching of arsenic from the contaminated material. In a preferred embodiment arsenic is transported into the leaf and/or stem tissue of the fern. Phosphorous "accumulating" plants have one or more of the above-listed characteristics with respect to phosphorous.

As used herein, reference to "fern plants" includes the Pteridophytes (true fern). Most fern plants are sporophytes which reproduce by means of spores. Fern plants typically produce masses of sporangia either on the underside of vegetative leaves or on specialized leaves that function only as reproductive structures. Specifically exemplified herein are fern plants of the orders Pteridales and Aspidiales and the families of Pteridaceae, Adiantaceae, Aspleniaceae, Dryopteridaceae, and Oleandraceae. Specifically exemplified genera are Adiantum, Asparagus, Asplenium, Cyrtomium, Didymochlacna, Dyropteris, Nephrolepis, Pteridium, Rumohra, and Pteris. The Pteris ferns are also known as Brake ferns. The specific examples of the Pteris ferns are *P. mayii, P. parkerii, P. albo-lineata*, and *P. vittata*.

Fern plants useful according to the subject invention can be readily identified by those skilled in the art. Useful guides to fern plants are readily available and include, for example, Lakela, Olga and Robert W. Long: "*Ferns of Florida*", An Illustrated Manual and Identification Guide" [1976], Banyan Books, Miami, Fla.); Jones, David L. (Encyclopedia of Ferns [1987], Lothian Publishing Company PTY LTD); and Snyder, Jr., Lloyd H. and James G. Bruce (Field Guide to the Ferns and Other Pteridophytes of Georgia" [1986] The University of Georgia Press).

Advantageously, the fern plants used in the present invention: (a) can be grown to high biomass; (b) are adaptable for growth in various agroclimatic conditions; (c) are adaptable to high-density culture; (d) are amenable to genetic manipulation by crossing, selection, mutagenesis and/or gene transfer. The excellent remediation properties presented herein are under field conditions and can be improved by optimization of field conditions as described herein, or by performing the remediation process in a controlled environment such as in a greenhouse. The conditions which can be manipulated to optimize performance in a given system include, pH, nutrients, water content, sunshine/shade, and amendments including chelators, organic amendments and inoculation of microorganisms. Optimization parameters, such as addition of nutrients (to support healthy plants) and amendments (to increase pollutant availability), apply to all fern plants, whereas others apply only to the Brake fern plants. The pH may be adjusted, for example, to be greater than 6.5 using liming materials such as limestone, dolomite, hydrated lime, burn lime, alkaline industrial wastes (e.g. ash and sludge), and phosphate rock. Essential macronutrients and micronutrients may also be applied including, for example, N, P, K, Ca, Fe, Mn, and Cu. The Brake fern plant is a hardy plant which shuns shade and revels in sunshine, and it requires free drainage but appreciates watering during dry periods. Additionally, chelators such as ethylene diamine tetraacetic acid (EDTA), dithylenetriaminpentaacetic acid (DTPA), nitrilotriacetic acid (NTA), citric acid, and oxalic acid and amendments such as compost, sewage sludge, and microorganisms (fungi) can be applied. Acidic environment (pH<6) and too much salt (over fertilization) can be detrimental to fern plant growth. The fern plants specifically exemplified herein are highly useful in removing arsenic from contaminated sites. In an alternative embodiment, the fern plants can be genetically manipulated to improve and/or expand their phytoremediation characteristics. See U.S. Pat. No. 6,005,092 to Shoseyou et al, which is incorporated by reference. Such characteristics may be for example the growth rate of the fern plants, the uptake rate of arsenic, and the hardiness of the plant. The genetic manipulation may be through, for example, traditional breeding techniques, mutagenesis, and/or genetic engineering. In a related embodiment, the genetic components responsible for the ability of fern plants to accumulate arsenic can be identified, isolated, and, if desired, transferred to another plant species thereby conferring on the transformed plant the ability to accumulate arsenic in useful levels. Alternatively, microorganisms and/or their genetic components involved in the arsenic removal process can be isolated and utilized.

In a specific embodiment, the subject invention provides an arsenic-accumulating fern plant. The Brake fern plot has been shown to accumulate up to and exceeding 7,500 mg/kg arsenic (dry weight) in its rachis (stems) and pinna (leaves). The arsenic concentrations in the soil where the plant has been studied range from 19 to 1,603 mg/kg. Thus, this plant has an extraordinary capability to enrich nearly 200 times more arsenic in its plant tissue than in the contaminated soil. Advantageously, the fern plants of the subject invention remove contaminants from soils having even low concentrations of pollutants. This is important for the process of the subject invention to lower the concentration of contaminants to an acceptable level.

The preferred methods of the invention involve growing one or more members of these plants under conditions sufficient for them to accumulate arsenic in their biomass. The term "arsenic" also includes mixtures, or compounds, comprising arsenic and organic or inorganic compounds.

The arsenic-containing environment into which these plants are introduced is not intended to limit the scope of the invention. That is, as long as the environment can sustain growth of fern plants, the environment can range from purely aquatic environments (i.e., hydroponic culture) to soil environments of varying degrees of water saturation, organic matter content, mineral content, and the like. Advantageously, fern plants can be grown in the sun or in the shade, and in either moist or dry environments. For example, the subject invention may be utilized in wetland. The pH can be as high as about 8–10 or even higher. It will be appreciated by those of ordinary skill in the art that the term "soil" can, therefore, include a wide variety of chemical and physical types. Thus, the materials from which pollutants can be removed according to the subject invention include soil, sediment, waste, and water.

The arsenic-accumulating fern plants suitable for the present methods extract arsenic from the environment into the roots of the fern plant. Preferably, the plants will translocate the arsenic from the roots into the shoots (i.e., the above-ground portions of the plant). The rates of accumulation can vary depending on a variety of factors, including the total arsenic concentration, soil type, pH, moisture content, organic matter content, soil temperature, planting density, and fertilizer use. With the teachings provided herein, the skilled artisan can readily select the preferred conditions for a particular application.

Generally, accumulation by the preferred fern plants can be as high as 100-fold or more above the levels present in the environment. The most preferred fern plant members accumulate several percent of arsenic as dry weight of shoot biomass and dried root biomass. Shoots or roots can then be harvested. The ability of the plants of the present invention to accumulate arsenic in the shoots is important because the shoots represent the harvestable (i.e., above-ground) biomass. The accumulation of arsenic in the shoots is preferred because generally roots are more difficult to harvest than shoots when the plants are grown in soil. However, any portion of the plant is potentially harvestable. For example, leaves, stems, fronds and roots may be harvested from fern plants.

In addition to arsenic contaminated soil, fern plant samples were also collected from uncontaminated sites, with arsenic concentrations ranging from 0.5 to 7.6 mg/kg. The arsenic concentrations in the frond (above-ground biomass) of these plants ranged from 12 to 64 mg/kg, with a maximum arsenic enrichment factor of 136. This clearly demonstrates that the fern plants of the subject invention accumulate arsenic from soils containing high as well as low arsenic levels.

Thus, the arsenic enrichment factor of fern plants is observed under natural growing conditions in contaminated as well as uncontaminated soils. The person skilled in the art, having the benefit of the current disclosure could optimize conditions for growth of the plants and uptakes of the pollutants. The uptake reported here is under conditions in the field and could be increased in an appropriately controlled environment such as a green house.

Arsenic conditions in common plants range from 0.01 to 5 mg/kg, with an average of 2.5 mg/kg. Thus, the fern plants of the subject invention accumulate as much as 3,000 times more arsenic than the average of common plants without suffering from arsenic toxicity. This is extremely unusual for a plant since arsenic has been used as a herbicide to control weeds.

The fern plants of the subject invention are highly advantageous for use in methods to remove arsenic from contaminated sites. These fern plants (*Pteris vittata*) are capable of surviving on a wide range of soil conditions, ranging from limestone surfaces to rock woodland. These fern plants also have a relatively large biomass; for example, these fern plants may produce a frond that is 30–90 cm in length, with blades of 25–60 cm long and 13–25 cm wide. Also, fern plants can be easily reproduced in tens of thousands from just one plant. Once planted in an arsenic contaminated soil, the fern plants of the subject invention come back every year because they are perennial plants, i.e., the fern plants can be harvested season after season until the site is cleaned up without reseeding or replanting.

In a specific embodiment, the subject invention concerns an arsenic accumulating Chinese brake fern plant (*Pteris vittata*). The average arsenic concentration in the soil where samples were collected was 394 mg/kg, with the highest arsenic concentration being 1,603 mg/kg. The average arsenic concentrations from eight plant samples in leaves, stems and roots were 4,359; 1,824; and 1,758 mg/kg dry weight, with the highest arsenic concentrations being 7,526 mg/kg in leaves. Based on the average arsenic concentration, the arsenic concentration in the fern was typically at least 5 times greater than that in soil. This plant is highly advantageous for extracting arsenic from arsenic contaminated soil, thus cleaning up the soil.

The arsenic accumulating fern plants of the subject invention can be used to remediate tens of thousands of arsenic contaminated soils nationwide and around the world. There are up to 10,000 arsenic contaminated sites in Florida alone. This technology is cost-effective and environmentally friendly and can be used by anyone who has to clean up arsenic contaminated sites. The remediation can be conducted in situ in the field or ex situ by removing the material to another location for a more controlled system. When the fern plants are harvested, the arsenic, phosphorous or other metal can be recovered or disposed of using methods know to those skilled in the art. The disposed or recovery step may include, for example, microbial treatment, chemical treatment, incineration, treatment with other plants, etc. These methods may further include the use of gasifiers.

The specific applications that this technique can be applied to arsenic contaminated environments include the following:

1. Cleanup Arsenic Contaminated Soils in Greenhouses

Arsenic herbicides are still currently used in several states, including Florida, New York, Georgia etc. As a result, many soils in greenhouses are contaminated with arsenic and need to be cleaned up;

2. Cleanup Arsenic Contaminated Groundwater or Surface Water

Arsenic contaminated groundwater or surface water can be pump up to irrigate the field where the fern plants grow to allow arsenic to be taken up by the fern plants and cleanup the groundwater;

3. Cleanup Soils Contaminated with Both Organics and Arsenic

Both fern plants (uptake arsenic and phosphorus) and poplar trees (help degrade organic contaminants) can be planted in the field to clean co-contaminated site;

4. Cleanup Soils Contaminated with Both Lead and Arsenic

Both fern plants (uptake arsenic and phosphorus) and India mustard (uptake lead) can be planted in the field to clean a co-contaminated site;

5. Cleanup Arsenic Contaminated Wetland

Fern plants can be planted to uptake both arsenic and phosphorus in a wetland environment;

6 Treat Wastewater

Fern plants can be grown in a field where wastewater can be used for irrigation to remove arsenic from the wastewater; and 7. Treat Waste Materials Fern plants can be grown directly in arsenic contaminated waste materials to cleanup the material.

In a specific embodiment the subject invention concerns a method of phytoremediating contaminated materials comprising cultivating fern plants in the materials containing contaminants under conditions sufficient to permit the fern plants to accumulate contaminants from the materials in the biomass of the fern plants such that the contaminants are at least 1% of the air-dried biomass of the fern plants. The fern plants can then be harvested and the contaminants recovered from the biomass. Preferably, the materials are conditioned to an optimized nutrient level to increase plant biomass and contaminants bioavailability. Sewage, sludge and compost can be added to promote fern plant growth. The contaminants include both organic and inorganic pollutants that are of environmental concern and include, but are not limited to, arsenic, phosphorous and other trace elements and heavy metals.

EXAMPLE 1

Site Characterization and Plant Analysis

Site description: An abandoned CCA wood preservative site located in central Florida was selected for a study. This site was operated from 1952 until 1962, pressure treating lumber in a cylinder 50 feet long and 6 feet in diameter with an aqueous solution of arsenic pentoxide, copper sulfate, and sodium or potassium chromate. From this activity, the site became heavily contaminated with arsenic, copper, and chromium. The average concentrations for this site are as follows: arsenic was present at a quantity of 361 mg/kg, 138 mg/kg chromium, and 67 mg/kg copper.

Soil Characterization: Sample grids consisted of 50 by 42-foot plots. Two sample grids that showed high levels of arsenic contamination were sampled. Three soil samples were collected from each site using a bucket auger and combined to give a representative sample. The soil was air dried and then screened to pass through a 2.0-mm sieve and thoroughly mixed before use. Soil pH was determined using 1:2 soil/water ratio and measured on a Fisher Scientific Accumet model 20 pH/conductivity meter. Soil organic matter was determined by the Walkley-Black method. Soil elemental analysis was conducted as follows: Approximately 1.0 g of air-dried soil was weighed into a 20 mL Teflon pressure digestion vessel to which 10 mL of concentrated nitric acid was added. Samples and reagent were mixed, sealed, and digested using a CEM MDS-2000 microwave sample preparation system for 10 minutes at 70 PSI (CEM 1991). Sample solutions were filtered and diluted to a final volume of 100 mL and stored in pre-cleaned polyethylene bottles in a refrigerator before analysis. Analysis for copper, chromium, and arsenic was conducted by graphite furnace atomic absorption on a Perkin Elmer SIMMA 6000 Simultaneous Multielement AA Spectrometer. Phosphorus, potassium, calcium, magnesium, iron, aluminum, and manganese were determined by an inductively coupled plasma spectrophotometer (ICP). These soil characteristics for the arsenic contaminated soil are presented in Table 2.

TABLE 2

Soil characterization of the CCA-contaminated site in Central Florida (mg/kg)

| Sample Sites | pH | OM | Al | Ca | Fe | P | K | Mg | As | Cu | Cr | Mn | Zn |
|---|---|---|---|---|---|---|---|---|---|---|---|---|---|
| Range | 7.4–7.6 | 0.5–0.8% | 1570–5920 | 260–37000 | 836–3670 | 40–820 | 30–300 | 60–240 | 39–1603 | 24–252 | 50–84 | 6–251 | 8–208 |
| Mean | 7.5 | 0.65% | 3421 | 6346 | 1765 | 193 | 84 | 241 | 361 | 138 | 67 | 45 | 101 |

Plant Analysis: Plant tissue samples were collected. The samples were rinsed, dried for 24 hours in a drying room, and ground using a Willey mill. Approximately 1.0 g of dried tree or plant material was weighed into a 20-mL Teflon pressure digestion vessel and mixed with 10 mL of concentrated nitric acid. Tissue samples were digested using a CEM MDS-2000 microwave sample preparation system for 5, 8, and 10 minutes at 40, 80, and 120 Psi respectively (CEM 1991). Sample solutions were diluted to a volume of 100 mL and stored in a refrigerator until analysis by graphite furnace atomic absorption using a Perkin Elmer SIMMA 6000 Simultaneous Multielement AA Spectrometer. Arsenic accumulation in the plant tissue was compared to the level of arsenic present in the soil. This was defined as the accumulation ratio or the phytoremediation coefficient.

Following are further examples that illustrate procedures for practicing the invention. Many examples used the soil materials collected from the above CCA contaminated site, which will be referred to as CCA contaminated soil. These examples should not be construed as limiting. All concentrations are by dry weight expressed as mg/kg unless otherwise noted.

EXAMPLE 2

Accumulation of Arsenic in Fern Plants

A species of arsenic accumulating plant was identified. The species, *Pteris vittata*, demonstrated an average accumulation of 4,360 mg/kg arsenic in its biomass in dry weight (Table 3). The Brake fern plant was not only tolerate to Cu (138 mg/kg) and Cr (67 mg/kg), but also taken up these two metals, but their levels were low compared to arsenic. Concentrations of Cu and Cr in these fern plants were generally greater than those of other species.

The results are presented in Table 3.

TABLE 3

Arsenic, copper and chromium levels in plant samples from the CCA contaminated site

| Common Name | Scientific Name | As | Cu | Cr |
|---|---|---|---|---|
| Southern Red Cedar | Juniperus silicola | 4.1 | 5.6–12 | 0.8–2.1 |
| Sugarberry | Celtis laevigata | 5.2 | 0.5–7.5 | 0.4–3.3 |
| Mockernut Hickory | Carya tomentosa | 9.9 | 3.6–7.5 | 0.7–6.3 |
| White Mulberry | Morus alba | 5.5 | 4.5–15 | 0.7–2.4 |
| Mimosa | Albizia julibrissin | 4.8 | 4.5–7.3 | 1.1–1.4 |
| Box-elder | Acer negundo | 9.2 | 10–14 | 0.9–1.9 |
| Poinsettia | Poinsettia heterophylla | 5.2 | 4.9–15 | 0.3–3.1 |
| Common Ragweed | Ambrosia artemissiiflora L. | 9.4 | 13–26 | 1.1–1.6 |
| Goldenrod | Solida sp. | 11.2 | 12–17 | 0.7–1.6 |
| Beggartick | Bidens alba L. | 8.0 | 7.1–15 | 0.5–2.1 |
| Brake Fern | Pteris vittata | 4,360 | 15–28 | 1.7–2.3 |

Two further collections of *P. vittata* were made to determine the accumulation of arsenic in the specific plant sections. Samples were collected, rinsed, and dried as before. After drying, the fern samples were separated into root, stem, and leave sections and digested by the previously described methodology. The results are given in Table 4.

TABLE 4

Arsenic Distribution by Plant Section in *P. vittata* in mg/kg

| Collection | Fern Plant Section | Range | Mean |
|---|---|---|---|
| I | Roots | 1152–3103 | 1758 |
| I | Stems | 383–2800 | 1824 |
| I | Leaves | 902–7526 | 4359 |
| II | Fronds | 3480–14540 | 9168 |

The mean concentration from collection I in the roots, stem and leaves were 1758, 1824, and 4359 mg/kg respectively.

EXAMPLE 3

Phytoremediation of Arsenic-contaminated Sites

The use of fern plants to remediate arsenic contaminated soils in the state of Florida is a feasible and cost effective technique. *P. vittata* is an introduced species that is common to South Africa, Asia, Japan, New Guinea, and Australia. In the United States, this species has been identified in Florida, Alabama, and Louisiana. The species can survive on a wide range of soil conditions, preferring to grow in areas that receive plenty of sun, basic soil conditions, and have free drainage. *P. vittata* has been identified growing on limestone formations, masonry mortar, rocky woodlands, canal banks, and often in disturbed sites. What makes this species so desirable for use in phytoremediating arsenic-contaminated soils is the fact that it produces a significant amount of above ground biomass, having fronds that grow between 30 to 90 cm long, with stipes that are 5 to 30 cm long. The fact that the largest mean accumulation of arsenic is in this section (mean stem and leaf concentrations of 1824 and 4359 mg/kg, Table 4) makes this species highly advantageous for remediation projects. The average arsenic concentration in the leaves was found to be 2 times or more greater than in the roots.

EXAMPLE 4

Effectiveness of Arsenic-accumulating Plant (*P. vittata*) in Contaminated and Non-contaminated Sites As shown in Tables 5–8, fern plants (*P. vittata*) which accumulate arsenic can be found at various locations including contaminated and non-contaminated sites.

TABLE 5

Arsenic concentrations in fern plants growing in the CCA contaminated site (mg/kg)

| | Arsenic concentrations | | | | Arsenic enrichment factor | | |
|---|---|---|---|---|---|---|---|
| Sample # | Leaves | Roots | Stems | Soil | Leaves | Roots | Stems |
| 2 | 902 | 2474 | 2800 | 18.8 | 48 | 132 | 149 |
| 3 | 1605 | 1152 | 1387 | 104 | 15 | 11 | 13 |
| 5 | 4548 | 3103 | 2745 | 66.1 | 69 | 47 | 42 |
| 6 | 3186 | 1851 | 2222 | 1603 | 2 | 1 | 1 |
| 7 | 3810 | 2576 | 1998 | 954 | 4 | 3 | 2 |
| 8 | 6236 | 1299 | 383 | 62.4 | 100 | 21 | 6 |
| 9 | 7060 | 1607 | 1909 | 308 | 23 | 5 | 6 |
| 10 | 7526 | N/A | 1152 | 38.9 | 193 | NA | 30 |
| Mean | 4359 | 1758 | 1824 | 394 | 11 | 4 | 5 |

N/A = Not available.

TABLE 6

Arsenic concentrations in the fern plants growing in the CCA and artificially contaminated soil after 8 weeks (mg/kg)

| Arsenic concentrations in soils (mg/kg) | 2 Weeks | 6 Weeks | 8 Weeks |
|---|---|---|---|
| Control soil (~6) | 755 | 438 | 539 |
| CCA soil (~400) | 3,525 | 6,805 | 5,519 |
| 50 | 5,131 | 3,215 | 4,120 |
| 500 | 7,849 | 21,290 | 13,961 |
| 1500 | 15,861 | 22,630 | |

TABLE 7

Arsenic concentration in the CCA and artificially contaminated soil after growing the fern plants for 8 weeks (mg/kg)

| Treatment | 2 Weeks | 6 Weeks | 8 Weeks | % Reduction |
|---|---|---|---|---|
| CCA soil | 489 | 361 | 272 | 44.4 |
| 50 | 48.1 | 24.1 | 29.9 | 38.0 |
| 500 | 519 | 317 | 218 | 58.0 |
| 1500 | 1932 | 657 | 258 | 86.6 |

TABLE 8

Non arsenic contaminated soil materials from 9 different locations at the University of Florida (mg/kg)

| | Arsenic concentrations | | Arsenic enrichment factor |
|---|---|---|---|
| Sample # | Frond | Soil | Frond |
| 1 | 64 | 0.47 | 136 |
| 2 | 11.8 | 3.65 | 3 |
| 3 | 13.28 | 1.68 | 8 |
| 4 | 42.1 | 2.37 | 18 |
| 5 | 38.4 | 2.84 | 14 |
| 6 | 16.2 | 7.56 | 2 |

TABLE 8-continued

Non arsenic contaminated soil materials from 9 different locations at the University of Florida (mg/kg)

| | Arsenic concentrations | | Arsenic enrichment factor |
|---|---|---|---|
| Sample # | Frond | Soil | Frond |
| 7 | 45.1 | 2.95 | 15 |
| 8 | 33.8 | 0.84 | 40 |

EXAMPLE 5

Effectiveness of Other Arsenic-accumulating Fern Plants in Removing Arsenic from Arsenic Contaminated Soils.

Various fern plants from different genus were grown in the previously described CCA-contaminated soils and two synthetically contaminated soils with arsenic concentrations of 50 and 500 mg/kg. These fern plants were purchased from several local nurseries except the Brake fern, which was cultivated in our lab from spores. The aboveground biomass of these fern plants were harvested after growing 2, 4, and 8 weeks. Samples were collected, rinsed, dried, digested, and analyzed as before. The results are given in Table 9 and Table 10. It is obvious that other fern plants species are also effective in accumulating a large amount of arsenic in their aboveground biomass, but not as effective as *P. vittata*. It seems that the genus Pteris is more effective in accumulating arsenic from arsenic contaminated soils.

TABLE 10-continued

Arsenic concentrations in the aboveground biomass of different fern plant species growing in the CCA (As = 245 mg/kg) and an artificially contaminated soil at the end of 8 weeks

| Common Name | Scientific Name | Arsenic concentrations (mg/kg) | | |
|---|---|---|---|---|
| | | Control | As = 245 | As = 50 |
| Asparagus | *Asparagus setaceus* | 0.06 | 15.4 | 2.33 |
| Sword | *Nephrolepis Cordifolia* | 0.07 | 7.53 | 16.5 |
| Leatherleaf | *Rumohra adiantiformis* | 0.27 | 5.57 | 11.3 |
| Bird's nest | *Asplenium nidus* | 0.03 | 2.47 | 2.65 |
| Foxtail | *Asparagus densiflorus* | 0.16 | 0.12 | 0.02 |
| Bracken | *Pteridium aquilinum* | 0.86 | 3.41 | — |
| Black stem | *Asplenium resiliens* | 0.56 | 11.7 | — |

EXAMPLE 6

Effectiveness of the Brake Fern Plant in Removing Arsenic from Different Arsenic Contaminated Soils.

The effectiveness of *P. vittata* in removing arsenic from arsenic contaminated soils from different contamination sources were tested. It was apparent that the Brake fern plant was effective in removing arsenic from all kinds of arsenic contaminated soils, including but not limited to contamination through mine tailing, lead-arsenate, and cattle dip vet.

Please keep in mind that the Brake fern plants grew in the soil matrix for only two weeks, yet they were able to accumulate significant amount arsenic in their aboveground biomass, 20.5 to 365 mg/kg compared to less than 5 ppm in other plants reported in the literature.

TABLE 9

Arsenic concentrations in the aboveground biomass of different fern plant species growing in the CCA (As = 245 mg/kg) and two artificially contaminated soils.

| Common name | Scientific name | Arsenic concentrations in the aboveground biomass (mg/kg) | | | | | | | | |
|---|---|---|---|---|---|---|---|---|---|---|
| | | wk 0 | As = 245 | | | As = 50 | | | As = 500 | | |
| | | | wk 2 | wk 4 | wk 8 | wk 2 | wk 4 | wk 8 | wk 2 | wk 4 | wk 8 |
| Mayii | *Pteris mayyii* | 0.54 | 270 | 2165 | 1268 | 3338 | 3802 | 2305 | 6617 | | 4405 |
| Parkerii | parkerii | 1.10 | 86 | 2213 | 1114 | 2201 | 5626 | 3847 | 4995 | | 2448 |
| Albo-lineata | *Pteris Albo-lineata* | 0.64 | 61 | 1355 | 2046 | 1542 | 1248 | 2036 | 2919 | | 1445 |
| Boston | *Nephrolepis exaltata* | 0.46 | 9 | 33 | 28 | 22 | | 85 | 3735 | | 948 |
| Autumn | *Dryopteris erythrosora* | 0.36 | 19 | 18 | 20 | 165 | | 154 | 1696 | | 4767 |

TABLE 10

Arsenic concentrations in the aboveground biomass of different fern plant species growing in the CCA (As = 245 mg/kg) and an artificially contaminated soil at the end of 8 weeks

| Common Name | Scientific Name | Arsenic concentrations (mg/kg) | | |
|---|---|---|---|---|
| | | Control | As = 245 | As = 50 |
| Brake | *P. Vittata* | 1.12 | 465 | 7.19 |
| Mayii | *P. Mayii* | 0.81 | 300 | 594 |
| Maidenhair | *Adiantum raddianum* | 0.22 | 46.6 | 109 |
| Silver Dollar | *Adiantum peruvianum* | 0.26 | 34.4 | 63.9 |
| Mahogany | *Didymochlacna truncatula* | 0.19 | 17.6 | 64.7 |
| Shield | *Dryopteris dilatata recurvata* | 0.05 | 20.4 | 40.4 |
| J. Holly | *Cyrtomium falcatum* | 0.11 | 20.1 | 40.1 |

It needs to point out that fern plants from three sources were used in various experiments. Some fern plants were collected from the CCA contaminated site and University of Florida campus, which had more mature rooting systems than those cultivated from our own lab. The Brake fern plants used in Example 6 (Table 11) were cultivated from our own lab from spores as in Example 5 (Table 10). Fern plants used in Example 2 (Tables 3 and 4) and Example 4 (Table 5) were from the CCA contaminated site located in Archer, Florida, whereas those in Example 4 (Tables 6, 7, 8, and 9) were collected from University of Florida campus. Given the same growing period, the fern plants that had more mature roots were able to accumulate more arsenic than those that were not. After two weeks, the fern plants collected from the campus (with more mature roots) were able to accumulate much more arsenic (3,525 mg/kg; Table 6) than those fern plants cultivated from our lab (75 mg/kg; Table 11). Given a longer growing season, for example 6–8 weeks, substantially more arsenic will be accumulated as demonstrated previously (Table 9).

It also needs to be noted that growing season could also make a difference. Substantially more arsenic were taken up by the Brake fern plants at relatively faster pace in the growing season than off growing season. The differences in arsenic accumulation by the Brake fern plant in Table 6 (during summer growing season, June to August) and Table 11 (during slow growing reason, February to March) could also be attributed to different growth of the fern plants. If this is the case, then the fact that more arsenic was taken up by the Brake fern plant from the mine tailing and Pb-arsenate contaminated soils than the CCA soil we have been testing is significant. This may imply that the Brake fern plant could not only survive in those adverse environments, but also were capable of accumulating large amount of arsenic.

TABLE 11

Arsenic concentrations in the aboveground biomass in *P. vittata* after growing in arsenic contaminated soils for two weeks except FP soils which were one week (mg/kg).

| Soil name | Contamination source | Soil level | Plant level |
|---|---|---|---|
| NB-S1 | Mine tailing | >500 | 184 |
| NB-S2 | Mine tailing | >500 | 365 |
| NB-C3 | Mine tailing | >500 | 192 |
| NB-C5 | Mine tailing | >500 | 325 |
| FP-U1 | Pb-arsenate/orchard | 50 | 100 |
| FP-U2 | Pb-arsenate/orchard | 50 | 76.9 |
| CCA | Wood treating site | 300 | 75.0 |
| Dudley Farm | Cattle dip site | 50 | 20.5 |
| Control | Garden soil | 0.8 | 0.57 |

EXAMPLE 7

Effectiveness of the Brake Fern Plants in Removing Arsenic from Different Arsenic Contaminated Wastes The effectiveness of *P. vittata* in removing arsenic from arsenic contaminated wastes were tested. It was apparent that the Brake fern plant was effective in removing arsenic from all kinds of arsenic contaminated wastes, including but not limited to different ashes, sawdust, different composts, and recovered screened materials. Given sufficient amount of time, more arsenic will be accumulated by the Brake fern plant, which was cultivated from our own lab and also used in Examples 5–11 (Tables 10–15).

TABLE 12

Arsenic concentrations in the aboveground biomass in *P. vittata* after growing in arsenic contaminated wastes for two weeks.

| Sample ID | Waste type | Waste level | Plant level |
|---|---|---|---|
| AS-10% | Coal/biomass ash | 150 | 47.5 |
| AS | Coal/biomass ash | 15 | 30.4 |
| TC | Papermill wood ash | 1 | 25.3 |
| Sawdust-10% | CCA treated lumber | 1,000 | 76.0 |
| Sawdust | CCA treated lumber | 10,000 | 163 |
| RelCo | Recycling compost | 1 | 2.73 |
| C&D | C&D compost | 1 | 1.35 |
| RSM | recovered screen material | 1 | 0.29 |
| Control | Garden soil | 0.8 | 0.57 |

EXAMPLE 8

Capability of the Brake Fern Plant in Removing Arsenic from Aqueous Solution

Hydroponic experiment was conducted to determine the capability of the Brake fern plant in removing arsenic from an aqueous solution with no soil. One fern plant (cultivated in our lab) was transplanted to a container with 200 mL of Hoagland's nutrient solution (25% strength, pH=7.5, three replicates) containing arsenic concentrations ranging from 1 to 100 mg/kg. The fern plant was harvested at the end of 20 days and analyzed for arsenic as previously described.

It was apparent that the Brake fern plant was extremely effective in removing arsenic from an aqueous solution containing arsenic concentrations of 1 to 100 ppm. The Brake fern plant was not only tolerate of arsenic concentration of 100 mg/kg, which will kill most plants, but also accumulated a large amount of arsenic in its aboveground biomass (up to 2,700 mg/kg). Arsenic concentrations in most contaminated soils will rarely exceed 100 mg/kg in aqueous solutions, which suggest that the Brake fern plant can be used in the most heavily contaminated soils. The aboveground arsenic concentrations in this fern plant were on the average 5 times greater than those in the roots, making this plant more appealing for phytoremediating arsenic contaminated materials since it is much easier to harvest aboveground biomass than roots. In addition, the arsenic was enriched in the aboveground biomass of this fern plant, with its minimum accumulation ratio (AR) of >30, i.e. arsenic concentrations in the plant were at least 30 times greater than those in the hydroponic solution. However, it was clear that arsenic AR decreased with increasing arsenic level in the matrix since the AR decreased from 105 to 30 as arsenic levels increased from 1 to 100 mg/kg.

TABLE 13

Arsenic accumulation by the Brake fern from aqueous solution containing arsenic of 1–100 mg/kg at the end of 20 days

| As level (mg/kg) | As level in plant (mg/kg) | | Ratio of Aboveground/ root | Accumulation ratio | |
|---|---|---|---|---|---|
| | aboveground | root | | aboveground | root |
| 1 | 118 | 22.0 | 54 | 105 | 20 |
| 10 | 651 | 222 | 2.9 | 70 | 24 |
| 50 | 2,424 | 480 | 5.1 | 53 | 10 |
| 100 | 2,715 | 602 | 4.5 | 30 | 6.5 |

EXAMPLE 9

Capability of the Brake Fern Plant in Removing Arsenic from an Artificially Contaminated Soil Containing Different Levels of Arsenic It has been shown that the Brake fern plant can tolerate up to 100 mg/kg arsenic in aqueous solution. This experiment determined the maximum arsenic concentration in an artificially contaminated soil, ranging from 50 to 500 mg/kg. One fern plant was transplanted to a pot containing 1.5 kg of the soil (four replicates), harvested after growing for 12 weeks and analyzed for arsenic as previously described.

The Brake fern plant was not only tolerant up to 500 mg/kg arsenic in the soil, but also accumulated a substantial amount of arsenic, especially in its aboveground biomass (up to 10, 536 mg/kg). The arsenic added to the soil was mostly water-soluble. Arsenic concentrations in the fern plant decreased with an increase in arsenic concentrations in the soil, with arsenic accumulation ratio decreasing from 64 to 21 as the soil arsenic concentrations increased from 50 to 500 mg/kg. Apparently this fern plant was more effective in enriching arsenic at a low concentration compared to a high one.

TABLE 14

Arsenic concentrations in the Brake fern after growing in an artificial contaminated soil for 12 weeks

| Treatment | Arsenic concentrations (mg/kg) | | Accumulation ratio | |
|---|---|---|---|---|
| (mg/kg) | Root | aboveground | Root | aboveground |
| Control (1) | 1.0 | 4.2 | 1.0 | 4.2 |
| 50 | 131 | 3,207 | 2.6 | 64 |
| 100 | 379 | 6,013 | 3.8 | 60 |
| 200 | 990 | 7,379 | 5.0 | 37 |
| 500 | 2,318 | 10,536 | 4.6 | 21 |

EXAMPLE 10

Capability of the Brake Fern Plant in Removing Arsenic from an Artificially Contaminated Soil Containing Different Species of Arsenic It has been demonstrated that the Brake fern plant was capable of accumulating arsenic from contaminated soils from various sources. This experiment determined the effectiveness of this fern plant in uptaking arsenic in an artificially contaminated soil spiked with 50 mg/kg of different species of arsenic. One fern plant was transplanted to a pot containing 1.5 kg of the soil (four replicates), harvested after growing for 18 weeks and analyzed for arsenic as previously described.

It is apparent that the Brake fern plant was effective in uptaking different arsenic species, including but not limited to those listed in Table 15, which are common pesticides used in the past (inorganic arsenic) and present time (organic arsenic). This fern plant was most effective in removing Ca—As and least effective in removing Al— and Fe—As, which could be related to their lower solubility compared to Ca—, Na—, and K—As.

TABLE 15

Arsenic concentrations in the Brake fern plant after growing in an artificially contaminated soil (As = 50 mg/kg) for 18 weeks

| | Arsenic concentrations (mg/kg) | | Accumulation ratio | |
|---|---|---|---|---|
| Arsenic species | Root | aboveground | Root | aboveground |
| Control (1) | 3.35 | 4.39 | 3.35 | 4.39 |
| Ca—As (V) | 190 | 2618 | 3.8 | 52 |
| Ca-MMA | 180 | 2212 | 3.6 | 44 |
| Na-MMA | 213 | 1771 | 4.3 | 35 |
| Na—As (III) | 390 | 1865 | 7.8 | 37 |
| K—As (V) | 373 | 1708 | 7.5 | 34 |
| Na—As (V) | 211 | 1665 | 4.2 | 33 |
| Al—As (V) | 178 | 315 | 3.6 | 6.3 |
| Fe—As (V) | 57.6 | 136 | 1.2 | 2.7 |

EXAMPLE 11

The Importance of Growth and Time in Arsenic Accumulation by the Brake Fern Plant How growth and time impact the effectiveness of the Brake fern plant in uptaking arsenic from the CCA contaminated soil (As=97.7 mg/kg, pH=7.9) was determined. One fern plant was transplanted to a pot containing 1.5 kg of the soil (four replicates), harvested after growing for 20 weeks and analyzed for arsenic as previously described.

Figure 1A:
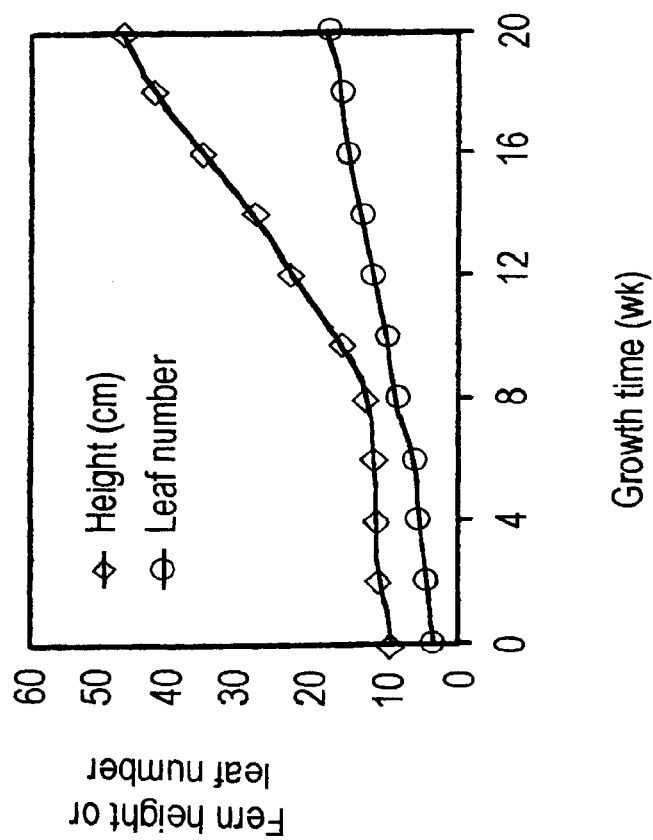
FIG. 1A is a graph of fern plant height or leaf number vs. growth time of Example 11.

Unlike the data presented in Table 6, the Brake fern plant didn't take up a substantial amount of arsenic within two weeks, which can be attributed to both slow growth (off growth season, October to February) and young root (cultivated in our lab). However, a substantial amount of arsenic was taken up by week 8, amounting to ~6,000 mg/kg, which was more 60 times greater than that of the soil (97.9 mg/kg). Another important point described earlier is that significantly more arsenic was accumulated in the aboveground biomass than in root biomass. FIGS. 1A and 1B show the comparison of the fern growth and its uptake of arsenic from the CCA contaminated soil

EXAMPLE 12

Phosphorus Accumulation from the CCA Contaminated Soil by the Brake Fern Plant

The fern samples were collected from the CCA contaminated site and analyzed for phosphorus. In addition to arsenic accumulation, the Brake fern plant was also effective in accumulating phosphorus from the CCA contaminated site as shown in Tables 16–17. As shown in Table 16 and 17 the Brake fern plants were shown to be effective in accumulating phosphorous.

TABLE 16

Phosphorous Concentration in Soil and the Fern Plant from the CCA Site in mg/kg

| | P Concentration | | | | Enrichment Factor | | |
|---|---|---|---|---|---|---|---|
| Sample # | Leaves | Roots | Stems | Soils | Leaves | Roots | Stems |
| 2 | 2,340 | 920 | 745 | 60 | 39 | 15 | 12 |
| 3 | 2,180 | 1,980 | 1,880 | 40 | 55 | 50 | 47 |
| 5 | 2,400 | 2,990 | 2,810 | 80 | 30 | 37 | 35 |
| 6 | 2,220 | 570 | 220 | 180 | 12 | 3 | 1 |
| 7 | 2,170 | 1,400 | 2,590 | 130 | 17 | 11 | 20 |
| 8 | 1,340 | 675 | 2,610 | 80 | 17 | 8 | 33 |
| 9 | 2,180 | 1,920 | 220 | 155 | 14 | 12 | 14 |
| 10 | 2,900 | N/A | 3,220 | 820 | 4 | N/A | 4 |

N/A = Not available.

TABLE 17

Phosphorous Distribution by Plant Section in *P vittata* in mg/kg

| Fern Section | Range | Mean | Enrichment Factor |
|---|---|---|---|
| Roots | 570–2990 | 1307 | 7 |
| Stems | 220–2810 | 1631 | 8 |
| Leaves | 1340–2400 | 1851 | 10 |
| Soil | 40–820 | 193 | |

Phosphorous enrichment factors ranged from 7 to 10 (Table 17).

While the invention has been described, disclosed, illustrated and shown in various terms of certain embodiments or modifications which it has presumed in practice, the scope of the invention is not intended to be, nor should it be deemed to be limited thereby and such other modifications or embodiments as may be suggested by the teachings herein are particularly reserved especially as they fall within the breadth and scope of the claims here appended.

We claim:

1. A process for removing a pollutant from a contaminated soil material wherein said process comprise the steps of:

planting a fern plant selected from the group consisting of Pteridaceae, Adiantaceae, Aspleniaceae, Dryopteridaceae, and Oleandraceae, on said soil material;

wherein said pollutant accumulates within biomass of the fern plant by phytoremediation to a level of at least 1% on a dry weight basis of the biomass of the fern plants, said pollutant selected from the group consisting of arsenic, copper and chromium, whereby the fern plant removes said pollutant from said soil material.

2. The process, according to claim 1, wherein said pollutant is arsenic.

3. The process according to claim 1, wherein said soil material further contains an additional pollutant selected from the group consisting of metals, trace elements, and phosphorous.

4. The process according to claim 3, wherein said additional pollutant is selected from the group consisting of phosphorous, lead, gold, selenium, cadmium, nickel, and zinc.

5. The process, according to claim 1, wherein said pollutant is chemically associated with at least one of an organic compound and an inorganic compound.

6. The process according to claim 1, wherein said soil material is selected from the group consisting of sediment in said soil, waste in said soil, and water in said soil.

7. The process according to claim 6, wherein said soil material is the sediment in said soil.

8. The process according to claim 6, wherein said soil material is the waste in said soil.

9. The process according to claim 6, wherein said soil material is the water in said soil.

10. The process according to claim 2, wherein arsenic accumulates in said plant in an amount greater than 100 mg/kg on a dry weight basis.

11. The process according to claim 10, wherein arsenic accumulates in said plant in an amount greater than 1000 mg/kg on a dry weight basis.

12. The process according to claim 10, wherein said arsenic accumulates in said plant in an amount greater than 10,000 mg/kg on a dry weight basis.

13. The process according to claim 2, wherein said arsenic accumulates in said plant to a concentration which is at least 2 times greater than the concentration of arsenic in the material from which the arsenic is being removed.

14. The process according to claim 13, wherein the concentration of arsenic is at least 10 times the concentration of arsenic in the material from which the arsenic is being removed.

15. The process according to claim 13, wherein the concentration of arsenic is at least 50 times the concentration of arsenic in the material from which the arsenic is being removed.

16. The process according to claim 13, wherein the concentration of arsenic is at least 100 times the concentration of arsenic in the material from which the arsenic is being removed.

17. The process, according to claim 2, wherein the arsenic concentration in the material from which the arsenic is being removed is greater than 5 milligrams per kilogram.

18. The process, according to claim 17, wherein the arsenic concentration in the material from which arsenic is being removed is greater than 50 milligrams per kilogram.

19. The process, according to claim 17, wherein the arsenic concentration in the material from which the arsenic is being removed is greater than 100 milligrams per kilogram.

20. The process, according to claim 17, wherein the concentration of arsenic in the material from which said arsenic is being removed is at least 500 milligrams per kilogram.

21. The process, according to claim 17, wherein the arsenic concentration in the material from which the arsenic is being removed is greater than 1,000 milligrams per kilogram.

22. The process according to claim 1, further comprising the step of:
removing the pollutant from at least a portion of said fern plant, the removal being selected from the group consisting of harvesting and disposing, and harvesting and recovering.

23. The process, according to claim 22, wherein said portion of said fern plant is selected from the group consisting of leaves, stems, fronds, and roots.

24. The process, according to claim 23, wherein said portion of said fern plant is the fronds.

25. The process, according to claim 1, wherein said fern plant is of the family Pteridaceae.

26. The process, according to claim 1, wherein said fern plant is of the family Adiantaceae.

27. The process, according to claim 26, wherein said fern plant is a *Adiantum raddianum*.

28. The process, according to claim 25, wherein said fern plant is of the genus Pteris.

29. The process, according to claim 28, wherein said fern plant is a *Pteris mayii*.

30. The process, according to claim 1, wherein said fern plant is a *Pteris parkerii*.

31. The process, according to claim 28, wherein said fern plant is a *Pteris albo-lineata*.

32. The process, according to claim 28, wherein said fern plant is a *Pteris vittata*.

33. The process, according to claim 1, wherein said process is conducted in a field.

34. The process, according to claim 1, wherein said process is conducted in a wetlands.

35. The process, according to claim 1, wherein said process is carried out in a greenhouse.

36. The process, according to claim 1, wherein said material has a pH of greater than 6.5.

37. The process, according to claim 36, wherein said pH is greater than 7.5.

38. The process, according to claim 36, wherein said pH is greater than 8.5.

39. The process according to claim 1, wherein said process further comprises prior to said planting the step of:
adding to said soil material a component which enhances the ability of said plant to accumulate said pollutant.

40. The process, according to claim 39, wherein said component is selected from the group consisting of pH adjusters, potassium, nitrogen, phosphorous, and chelators.

41. The process, according to claim 40, wherein said pH adjusters is selected from the group consisting of limestone, dolomite, hydrated lime, burnt lime, alkaline wastes, and phosphate rock.

42. The process, according to claim 40, wherein said chelator is selected from the group consisting of EDTA, DTPA, NTA, citric acid, and oxalic acid.

43. The process according to claim 1, wherein said process further comprising prior to said planting
treating said soil material to improve the removal of said pollutants from said soil material.

44. The process according to claim 43, wherein said treating is selected from the group consisting of chemical treating, incinerating, treating with other plants, and treating with microorganisms.

45. A process for recovering a pollutant present in a soil material comprising the steps of:

planting a fern plant selected from the group consisting of Pteridiaceae, Adiantaceae, Aspleniaceae, Dryopteridaceae, and Oleandraceae, on said soil material;

wherein the pollutant accumulates within biomass of the fern plant by phytoremediation, the pollutant selected from the group consisting of arsenic, copper and chromium, such that said pollutant accumulates in portions of said fern plant, said portions selected from the group consisting of leaves, stems, fronds and roots.

46. The process according to claim 45, wherein said soil material contains an additional pollutant selected from the group consisting of trace elements and metals.

47. The process according to claim 46, wherein said additional pollutant is selected from the group consisting of gold and arsenic.

48. The process, according to claim 45, wherein said process further comprises at least one step selected from the group consisting of microbial treating, chemical treating, and incinerating.

49. A method of phytoremediating arsenic containing soil material comprising the steps of:

planting a fern plant in said soil material, the fern plant selected from the group consisting of Pteridiaceae, Adiantaceae, Aspleniaceae. Dryopteridaceae, and Oleandraceae;

wherein the fern plant accumulates a concentration of arsenic by phytoremediation; and harvesting said plant, whereby said arsenic containing soil material has a reduced arsenic content.

50. A method of phytoremediating soil material containing a pollutant selected from the group consisting of copper and chromium, comprising the steps of:

planting a fern plant in said soil, the fern plant selected from the group consisting of, *Pteridiaceae, Adiantaceae, Aspleniaceae, Dryopteridaceae, and Oleandraceae*; wherein the fern plant accumulates a concentration of said pollutant by phytoremediation; and harvesting said plant, whereby said pollutant containing said material has a reduced pollutant content.

* * * * *